United States Patent [19]

Nahm et al.

[11] 4,391,995
[45] Jul. 5, 1983

[54] 4-PHENOXY-PHENOXY-ALKANE-CARBOXYLIC ACID DERIVATIVES AND PROCESS FOR THEIR MANUFACTURE

[75] Inventors: Helmut Nahm; Ernold Granzer, both of Kelkheim, Fed. Rep. of Germany

[73] Assignee: Hoechst Aktiengesellschaft, Frankfurt am Main, Fed. Rep. of Germany

[21] Appl. No.: 265,902

[22] Filed: May 21, 1981

Related U.S. Application Data

[60] Division of Ser. No. 179,889, Aug. 20, 1980, Pat. No. 4,301,295, which is a continuation-in-part of Ser. No. 905,049, May 11, 1978, Pat. No. 4,238,626, which is a continuation-in-part of Ser. No. 542,061, Jan. 17, 1975, abandoned, which is a continuation of Ser. No. 273,770, Jul. 21, 1972, abandoned.

[30] Foreign Application Priority Data

Jul. 23, 1971 [DE] Fed. Rep. of Germany ....... 2136828

[51] Int. Cl.³ .............................................. C07C 2/88
[52] U.S. Cl. .................................................. 568/637
[58] Field of Search ........................... 560/62; 568/637

[56] References Cited

FOREIGN PATENT DOCUMENTS 2000174 8/1969 France .................................... 560/62
6401526 8/1964 Netherlands .

Primary Examiner—Paul J. Killos
Attorney, Agent, or Firm—Curtis, Morris & Safford

[57] ABSTRACT

Novel 4-phenoxy-phenoxy-alkane-carboxylic acid derivatives of the formula I

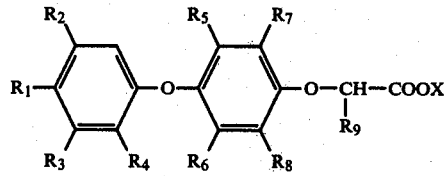

in which
$R_1$ stands for hydrogen, methylithio, cyclopentyl, cyclohexyl, phenyl, methylcycylohexyl, ethylcyclohexyl, or $R_1$ and $R_3$ together stand for a —CH=CH—CH=CH— bridge or—unless at least one of the substituents $R_2$ to $R_8$ stands for hydrogen, or if $R_9$ stands for a radical having at least 2 carbon atoms—for chlorine,
$R_2$ and $R_3$, independent of one another, each stands for hydrogen, chlorine or alkyl of 1 to 4 carbon atoms,
$R_4$ stands for hydrogen, chlorine, alkyl of 1 to 4 carbon atoms, cyclopentyl, cyclohexyl, methylcyclohexyl or $R_3$ and $R_4$ together stand for a —CH=CH—CH=CH— bridge,
$R_5$, $R_6$ and $R_7$, independent of one another, each stands for hydrogen or alkyl of 1 to 4 carbon atoms,
$R_8$ stands for hydrogen, alkyl of 1 to 4 carbon atoms or allyl,
$R_9$ stands for alkyl of 1 to 10 carbon atoms or phenyl and
X stands for hydrogen, the cation of a physiologically acceptable inorganic or organic base of a hydrocarbon radical of 1 to 10 carbon atoms, having a strong action on the lipide and cholesterine metabolism and a process for this manufacture.

1 Claim, No Drawings

4-PHENOXY-PHENOXY-ALKANE-CARBOXYLIC ACID DERIVATIVES AND PROCESS FOR THEIR MANUFACTURE

This application is a divisional of application Ser. No. 179,889 filed Aug. 20, 1980, now U.S. Pat. No. 4,301,295, which latter application is in turn a continuation-in-part of application Ser. No. 905,049 filed May 11, 1978, now U.S. Pat. No. 4,238,626 which in turn is a continuation-in-part of application Ser. No. 542,061 filed Jan. 17, 1975 (now abandoned), which in turn is a continuation of application Ser. No. 273,770 filed July 21, 1972 (now abandoned).

The present invention relates to novel 4-phenoxy-phenoxyalkane-carboxylic acid derivatives having a strong action on the lipide and cholesterine metabolism and corresponding to the formula I

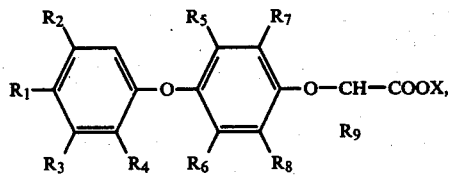

in which
$R_1$ stands for hydrogen, methylthio, cyclopentyl, cyclohexyl, phenyl, methyl-cyclohexyl, ethyl-cyclohexyl, or $R_1$ and $R_3$ together stand for a —CH=CH—CH=CH— bridge or—unless at least one of the substituents $R_2$ to $R_8$ stands for hydrogen, or if $R_9$ is a group of at least 2 carbon atoms—for chlorine,
$R_2$ and $R_3$, independent of one another, each stands for hydrogen, chlorine or alkyl of 1 to 4 carbon atoms,
$R_4$ stands for hydrogen, chlorine, alkyl of 1 to 4 carbon atoms, cyclopentyl, cyclohexyl, methyl-cyclohexyl or $R_3$ and $R_4$ together stand for a —CH=CH—CH=CH— bridge,
$R_5$, $R_6$ and $R_7$, independent of one another, each stands for hydrogen or alkyl of 1 to 4 carbon atoms,
$R_8$ stands for hydrogen, alkyl of 1 to 4 carbon atoms or allyl,
$R_9$ stands for alkyl of 1 to 10 carbon atoms or phenyl and
X stands for hydrogen, the cation of a physiologically acceptable inorganic or organic base or a hydrocarbon radical of 1 to 10 carbon atoms.

This invention also relates to a process for the manufacture of 4-phenoxy-phenoxy-alkane-carboxylic acid derivatives of the formula I, which comprises reacting a 4-phenoxy-phenol of the formula II

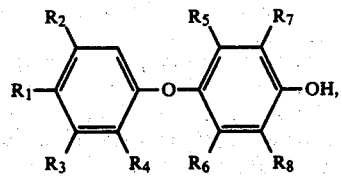

in which $R_1$ to $R_8$ are defined as above, with an α-halogeno-fatty acid derivative of the formula III

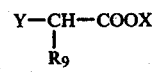

in which $R_9$ stands for alkyl of 1 to 10 carbon atoms or phenyl and X stands for hydrogen, the cation of a physiologically acceptable inorganic or organic base or a hydrocarbon radical of 1 to 10 carbon atoms, and Y stands for a halogen atom, preferably chlorine or bromine, in the presence of a compound capable of splitting off hydrogen halide, and where required saponifying the 4-phenoxy-phenoxy-alkane-carboxylic acid ester obtained with an alkaline agent or esterifying the 4-phenoxy-phenoxy-alkane carboxylic acid obtained or transesterifying a 4-phenoxy-phenoxy-alkane-carboxylic acid ester of the formula I, in which $R_1$ to $R_9$ are defined as above and X stands for alkyl of 1 to 3 carbon atoms, with an alcohol having 4 to 10 carbon atoms.

The 4-phenoxy-phenols of the formula II may be obtained according to at least one of the following methods:

(a) A phenol of the general formula IV

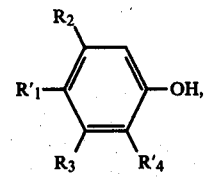

is reacted with a substituted 4-halogeno-anisole of the formula V

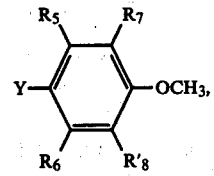

in the presence of an alkaline agent and copper to yield a compound of the formula VI

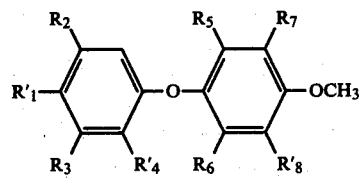

in which formulae IV, V and VI $R'_1$ stands for hydrogen, cyclohexyl, phenyl, methyl-cyclohexyl or ethylcyclohexyl, or—unless at least one of the substituents $R_2$ to $R_8$ is hydrogen, or if $R_9$ is a radical of at least 2 carbon atoms—for chlorine, $R_2$ and $R_3$, independent of one another, each is hydrogen, chlorine or alkyl of 1 to 4 carbon atoms, $R'_4$ is hydrogen, alkyl of 1 to 4 carbon atoms, cyclopentyl, cyclohexyl, or $R'_4$ together with $R_3$ is a —CH=CH—CH=CH— bridge, $R'_8$ is hydrogen or alkyl of 1 to 4 carbon atoms, and $R_2$, $R_3$, $R_5$, $R_6$ and $R_7$ are defined as above and Y is halogen.

According to this reaction, the alkali metal phenolate is formed first at a temperature of from 180° to 190° C., while water is split off, and it is then reacted with the compound of the formula V, while the alkali metal halide which is insoluble in the melt is split off. After a reaction time of 3 to 4 hours, the cooled reaction mixture is extracted with methylene chloride which does not dissolve the inorganic salts formed. In order to remove unreacted portions of the phenol of the formula IV, the methylene chloride solution is shaken several times with 2 N sodium hydroxide solution. After the solvent has been distilled off, the residue is distilled in vacuo. The compounds of the formula VI, thus obtained in a 50 to 60% yield, are dealkylated by means of hydrogen bromide in glacial acetic acid to yield the corresponding 4-phenoxy-phenols.

Starting substances, in which $R_1$ to $R_7$ are defined as above for formula I and $R_8$ stands for hydrogen or alkyl of 1 to 4 carbon atoms, may be prepared according to method (b);

(b) A phenol of the formula VII

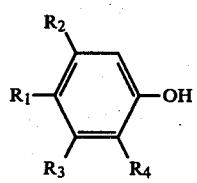

is reacted in dimethylformamide with 4-nitro-chlorobenzene in the presence of an alkali metal carbonate and copper to yield the correspondingly substituted phenoxy-nitrobenzene of the formula VIII

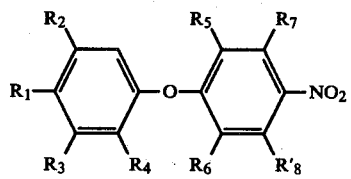

After reduction with catalytically activated hydrogen, the corresponding aniline is diazotized with nitrous acid and reacted with hydrofluoboric acid to yield the sparingly soluble salt of the formula IX

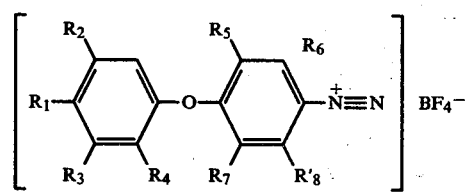

This salt is reacted in boiling acetic acid anhydride to yield the corresponding acetoxy-phenol which is converted, after the acetyl group has been split off with an alkaline agent, into the free phenol of the formula X

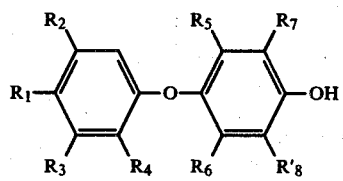

The starting substances which carry the allyl group as substituent $R_8$, are prepared according to method (c):

(c) A phenoxy-phenol of the formula X, in which $R'_8$ is hydrogen, is first reacted with allyl bromide in the presence of potassium carbonate to yield the corresponding allyl ether. After the rearrangement according to Claisen at 190°–200° C., there is obtained an allyl-phenol substituted in ortho-position, which may be converted into n-propylphenol by reduction.

A so-obtained phenoxy-phenol of the formula II is reacted with a substantially equimolar amount, or with a slight excess of up to about 10 percent, of an α-halogeno-fatty acid ester of the formula III, advantageously in a polar organic solvent. As halogeno-fatty acid esters, there are suitably used esters having an unbranched alkyl group $R_9$ or the esters of α-halogeno-phenylacetic acid.

As solvents, there are used ketones such as acetone or butanone; ethers such as tetrahydrofuran, methoxybutanol, or ethylene-diglycol dimethyl ether; aromatic substances such as benzene or toluene; or carboxylic acid amides, such as dimethylformamide or dimethylacetamide. For binding the hydrogen halide that has been split off, an alkaline compound, such as potassium carbonate, sodium carbonate, magnesium oxide, or a tertiary organic base, such as triethylamine, is added.

In a variation of this process, the phenoxyphenol is first transformed into its phenolate by stirring or heating it for a short time with excess aqueous alkali in a non-polar organic solvent such as benzene, toluene, or xylene at temperatures between room temperature and about 50° C. Water is removed by conventional methods such as azeotropic distillation and the residual organic suspension is heated with methyl 2-halopropionate for 1 to 12 hours at temperatures between 80° C. or—in the case of methyl 2-chloro-propionate—between 100° C. and reflux temperature.

When the reaction is complete, the dissolved product is separated by suction-filtration from the salt of the hydrohalic acid formed. After the organic solvent has been distilled off, the ester formed is isolated and purified by distillation.

Where required, a carboxylic acid ester thus obtained is treated with an alkaline agent for saponification, advantageously using aqueous alkaline solutions, in the present of low-molecular-weight alcohols, and refluxing for up to 3 hours. The alkaline solution is then acidified, whereupon the free acid precipitates in a crystallized or oily form.

When a phenoxy-phenol of the formula II is reacted with an α-halogeno-fatty acid of the formula II or with a salt thereof, the reaction is suitably carried out in an aqueous strongly alkaline solution, for example in a potassium hydroxide solution, sodium hydroxide solution or calcium hydroxide solution. It is advantageous to add the α-halogen-fatty acid to the alkaline solution of the phenoxy-phenol, whereupon the corresponding salts of 4-phenoxy-phenoxy-alkane-carboxylic acid precipitate together with the corresponding salt of hydrohalic acid. After addition of a dilute mineral acid, such as hydrochloric acid or sulfuric acid, the free 4-phenoxy-phenoxy-alkane-carboxylic acid precipitates, in most cases, in an oily form, preferably upon heating at 50°–90° C., while the salt of the hydrohalic acid enters into solution. Upon cooling the 4-phenoxy-phenoxy-alkane-carboxylic acid crystallizes and can be purified by recrystallization from water or water-containing solvents, for example dilute acetic acid.

Where required, the free 4-phenoxy-phenoxy-alkane-carboxylic acids of the formula I may be esterified in usual manner, preferably in the presence of catalytic amounts of an acid such as sulfuric acd, toluene-sulfonic acid or hydrochloric acid. For the esterification, for example, there may be mentioned the following alcohols: aliphatic linear or branched alcohols having up to 10 carbon atoms, in particular methyl alcohol, ethyl alcohol, propyl alcohol or isopropyl alcohol, cycloaliphatic alcohols, such as cyclohexanol or cyclopentanol, araliphatic alcohols such as benzyl alcohol or phenylethyl alcohol, in which the phenyl ring may also be substituted by alkoxy groups, or terpine alcohols, such as borneol, fenchol or terpineol.

To bring about esterification the easily obtainable acid chlorides of 4-phenoxy-phenoxy-alkane-carboxylic acids may be also reacted with said alcohols, the acid chlorides being prepared, for example, by reacting the acids with thionyl chloride.

Moreover, 4-phenoxy-phenoxy-alkane-carboxylic acid esters of higher alcohols may be obtained by transesterification of lower alkyl esters. Transesterification is advantageously performed in an excess amount of the higher-boiling alcohol desired and the lower alcohol set free is continuously distilled off.

The 4-phenoxy-phenoxy-alkane-carboxylic acid derivatives of the invention may be used as medicaments both in the form of the free acids and in the form of the esters or salts thereof with physiologically acceptable bases. As salts, there are especially mentioned salts of sodium, potassium, ammonium or of ethanolamine, ethylene-diamine, diethylamine, dimethylamine, piperidine or morpholine. As ester components, there are preferred linear or branched alcohols having 1 ro 4 carbon atoms, cyclopentyl, cyclohexyl or benzyl alcohol.

The 4-phenoxy-phenoxy-alkane-carboxylic acid derivatives have a very strong action on the lipide and cholesterine metabolism.

The reduction of increased lipide values in the blood serum is of great importance for the prophylaxis and therapy of arteriosclerotic diseases. The novel compounds of the invention may be applied in the form of pharmaceutical compositions, in admixture with usual carriers and adjuvants, for the reduction of the serum lipide values; an oral administration being preferred.

The action of the compounds of the invention was tested as follows: Prior to the treatment, blood was taken from various groups of 10 rats each and the total content of cholesterine in the serum was determined according to the method of Richterich and Lauber; moreover, the triglycerides were determined by the enzymatical method of kreutz and Eggstein. Subsequently, the compounds of the invention cited in the following Table were administered to the animals once per day in the indicated dosage units by means of an oesophagal sound. 24 hours after the last one of 8 dosage units had been administered, blood samples were again taken from the animals and cholesterine and triglycerides were determined in the serum. In the following Table, the changes in percentage of the cholesterine and triglyceride values are referred, on the one hand, to the average value of the lot prior to the treatment (before the dash), on the other hand, the values after the treatment are referred to the values obtained at the same time from the untreated control animals (after the dash). The control lot also comprised 10 rats. The corresponding reference value without a treatment was defined as being 100%.

It appears that the compounds of the invention bring about a substantial reduction both of the cholesterine values and of the triglyceride values in the blood serum.

TABLE

| Compound of Example | 8 Dosage units administered per os each comprising | | | |
|---|---|---|---|---|
| | 30 mg/kg/day | | 10 mg/kg/day | |
| | reduction of chloesterine in % | reduction of triglyceride in % | reduction of cholesterine in % | reduction of triglyceride in % |
| No.2 | −42/−29 | −43/−32 | | |
| No. 3 | −45/−36 | −43/−35 | −24/−29 | −14/ |
| No. 5 | −24/−8 | −25/−17 | −18/ | −21/ |
| No. 8 | −25/ | −25/ | −35/ | −10/ |
| No. 10 | −15/ | −44/ | −16/−7 | −33/ |
| No. 13 | | −50/−55 | −28/−18 | −37/−38 |
| No. 16 | −18/−25 | −33/−15 | −7/−25 | −43/−27 |
| No. 17 | −29/−13 | −30/−20 | −21/−15 | −41/−23 |
| No. 24 | −6/−15 | −20/−15 | −19/−8 | −26/−26 |
| No. 33 | −12/−17 | −51/−14 | −13/−9 | −43/−8 |

As further taught in U.S. Pat. No. 3,954,442 granted May 4, 1976, the compounds of the present invention also show an excellent selective herbicidal effect against weed grasses in crop plants, particularly cereals and dicotyledenous crops.

The following Examples serve to illustrate the invention.

EXAMPLES 1. 4(4-chlorophenoxy)-α-phenoxy-caproic acid

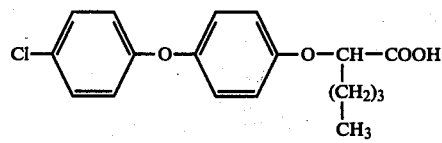

(a) A solution of 64 g of 4(4-chlorophenoxy)-phenol and 80 g of α-bromocaproic acid ethyl ester in 100 ml of butanone was heated at the boil for 10 hours, while stirring, with 100 g of potassium carbonate. After inorganic salts had been filtered off, the filtrate was vaporized to dryness, the ester formed was dissolved in methylene chloride and isolated, after being shaken several times with water, by vaporization of the organic solvent. It was purified by distillation in vacuo. 52 g of 4(4-chloro-phenoxy)-α-phenoxy-caproic acid ethyl ester were obtained, boiling point 223°–225° C. under a pressure of 3 mm mercury.

(b) 52 g of the ester obtained were refluxed for 2 hours on a steam bath with 300 ml of methanol and 30 ml of 45% sodium hydroxide solution. Excess solvent was removed in vacuo and the remaining sodium salt of 4(4-chlorophenoxy)-α-phenoxy-caproic acid was dissolved in water. After acidification with concentrated hydrochloric acid, the acid precipitated first in an oily form and then crystallized. It could be recrystallized from 80% acetic acid. 35 g of 4(4-chlorophenoxy)-α-phenoxy-caproic acid were obtained, m.p. 94° C. (corrected).

In an analogous manner, the following compounds were prepared by a reaction of equivalent amounts of phenol and α-halogeno-fatty acid ester. (All the melting points are corrected).

2. 4(4-Chlorophenoxy)-α-phenoxy-caprylic acid, m.p. 70° C.

3. 4(4-Chlorophenoxy)-α-phenoxy-capric acid, m.p. 66° C.
4. 4(4-Chlorophenoxy)-α-phenoxy-lauric acid, m.p. 64° C.
5. 4(4-Chloro-2-cyclohexylphenoxy-α-phenoxy-propionic acid benzylamine salt (acid in oily form), m.p. 145° C.
6. 4(4-Chlorophenoxy)-α-2-propylphenoxy-propionic acid dicyclohexylamine salt (acid in oily form), m.p. 156° C.
7. 4(4-Chlorophenoxy)-α-2-allylphenoxy-propionic acid dicyclohexylamine salt (acid in oily form), m.p. 173° C.
8. 4(4-Chloro-2-cyclopentyl-phenoxy)-α-phenoxy-propionic acid benzylamine salt (acid in oily form), m.p. 138° C.
9. 4(4-(4-Methylcyclohexylphenoxy)-α-phenoxy-propionic acid dicyclohexylamine salt (acid in oily form), m.p. 112° C.
10. 4(2-(4-Methylcyclohexylphenoxy)-α-phenoxy-propionic acid cyclohexylamine salt (acid in oily form), m.p. 148° C.
11. 4(2-Tert.butyl-5-methyl-phenoxy)-α-phenoxy-propionic acid, m.p. 78° C.
12. 4(4-Tert.-butyl-2-methyl-phenoxy)-α-phenoxy-propionic acid, m.p. 118° C.
13. 4(2-Cyclohexyl-5-methylphenoxy)-α-phenoxy-propionic acid benzylamine salt (acid in oily form), m.p. 146° C.
14. 4(2-Cyclohexylphenoxy)-α-phenoxy-propionic acid benzylamine salt (acid in oily form), m.p. 144° C.
15. 4(4-Cyclohexyl-phenoxy)-α-phenoxy-propionic acid m.p. 126° C.
16. 4(2-Isopropyl-5-methylphenoxy)-α-phenoxy-propionic acid, m.p. 92° C.
17. 4(2,4-Dichlorophenoxy)-α-phenoxy-propionic acid, m.p. 112° C.
18. 4(4-Chloro-3,5-dimethylphenoxy)-α-2,6-dimethylphenoxy-propionic acid, m.p. 48° C.
19. 4(4-Chlorophenoxy)-α-2,6-dimethylphenoxy-propionic acid, m.p. 120° C.
20. 4(4-Methylphenoxy)-α-phenoxy-propionic acid, m.p. 91° C.
21. 4(3-Methylphenoxy)-α-phenoxy-propionic acid, m.p. 79° C.
22. 4(4-Chloro-3-methylphenoxy)-α-phenoxy-propionic acid, m.p. 129° C.
23. 4(4-Chloro-2-methylphenoxy)-α-2,6-dimethylphenoxy-propionic acid benzylamine salt (acid in oily form), m.p. 136° C.
24. 4(4-Chloro-3,5-dimethylphenoxy)-α-3,5-dimethylphenoxy-propionic acid, m.p. 160° C.
25. 4(4-Phenylphenoxy)-α-phenoxy-propionic acid, m.p. 138° C.
26. 4(3,4-dichlorophenoxy)-α-phenoxy-propionic acid, m.p. 119° C.
27. 4(2-Chlorophenoxy)-α-phenoxy-propionic acid, m.p. 106° C.
28. 4(1-Naphthyloxy)-α-phenoxy-propionic acid, m.p. 146° C.
29. 4(2-Naphthyloxy)-α-phenoxy-propionic acid, m.p. 138° C.
30. 4(4-Chlorophenoxy)-α-phenoxy-phenyl-acetic acid, m.p. 136° C.
31. 4(4-Phenyl-phenoxy)-α-phenoxy-phenyl-acetic acid, m.p. 156° C.
32. 4(4-Chloro-3-methylphenoxy)-α-phenoxy-phenyl-acetic acid, m.p. 114° C.
33. 4(2,4-Dichlorophenoxy)-α-phenoxy-phenyl-acetic acid, m.p. 122° C.
34. 4(3,5-Dichloro-phenoxy)-α-phenoxy-propionic acid, m.p. 131° C.
35. 4-(2',4'-dichlorophenoxy)-α-phenoxy-propionic acid isopropyl ester

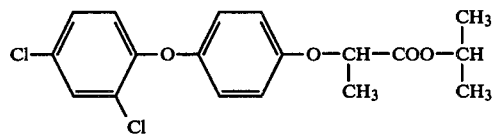

55 g of 4-(2',4'-dichlorophenoxy)-α-phenoxy-propionic acid were suspended in 500 ml of isopropanol. While stirring, hydrogen chloride was fed in, whereupon the temperature rose to about 50° C. While the feed of hydrogen chloride was continued, the suspension was refluxed for 5 hours and the reaction mixture was then allowed to stand overnight. After the excess alcohol had been distilled off, the solution was poured on water and then extracted with methylene chloride. The methylene chloride extract was washed with dilute bicarbonte solution and then twice with water and dried over sodium sulfate. After filtration the solution was concentrated and then distilled under greatly reduced pressure. 34 g of 4-(2',4'-dichlorophenoxy)-α-phenoxy-propionic acid isopropyl ester were obtained, boiling point 182°–185° C. under a pressure of 0.04 mm mercury.

36. In a manner analogous to Example 35, the 4-(2',4'-dichlorophenoxy)-α-phenoxy-propionic acid isobutyl ester

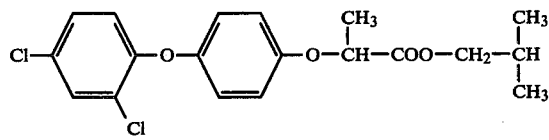

boiling point: 180°–185° C./0.12 mm mercury, was obtained.

37. α-4(2',4'-dichlorophenoxy)-phenoxy-propionic acid cyclohexyl ester

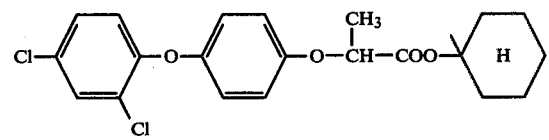

50 g of α-4(2',4'-dichlorophenoxy)-phenoxy-propionic acid ethyl ester, 1 g of p-toluene-sulfonic acid and 250 ml of cyclohexanol were carefully heated at the boil. The ethyl alcohol formed distilled off. After 3 hours, the reaction mixture was dissolved in 400 ml of methylene chloride, shaken once with 2 N ammonia solution and several times with water. After the organic phase had been vaporized, the residue was distilled in vacuo. 50 g of α-4-(2',4'-dichlorophenoxy)-phenoxy-propionic acid cyclohexyl ester were obtained, boiling point 236°–240° C./1 mm mercury.

In a manner analogous to Example 37, there were obtained

38. α-4-(2',4'-dichloro-phenoxy)-phenoxy-propionic acid 4-methyl-cyclohexyl ester

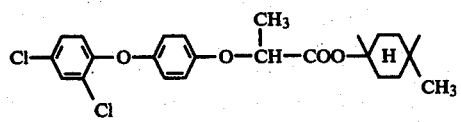

boiling point: 245°-250° C./1 mm mercury, and
39. α-4(2',4'-dichlorophenoxy)-phenoxy-propionic acid cyclopentyl ester

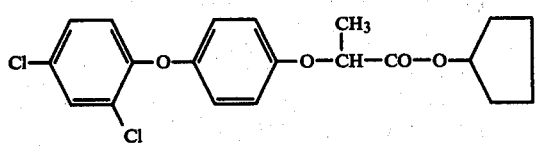

boiling point: 220°-230° C./1 mm mercury.
40. 4(4-methylthio-phenoxy)-phenoxy-acetic acid ethyl ester

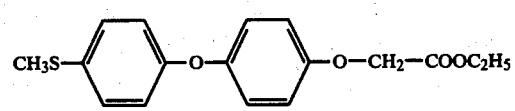

(a) While stirring, 30 g of 4(4-methylthio-phenoxy)-phenol were dissolved in 350 ml of methylethyl-ketone. After addition of 18 g of potassium carbonate and 16 g of chloroacetic acid ethyl ester, the mixture was heated at the boil for 8 hours. Inorganic components were then separated by suction-filtration. After vaporization of the organic solvent, the residue was dissolved in 300 ml of methylene chloride and the solution was shaken several times with water. The organic phase was vaporized and the residue was distilled in vacuo. 25 g of 4(4-methylthio-phenoxy)-phenoxy-acetic acid ethyl ester were obtained, boiling point: 215°-230°/3-4 mm mercury.
4(4-methylthio-phenoxy)-phenoxy-acetic acid

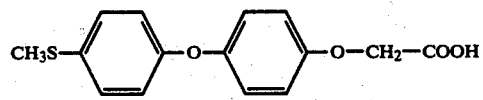

(b) 25 g of the above-cited ester were dissolved in 250 ml of methanol and, after addition of 25 ml of 45% sodium hydroxide solution, the mixture was refluxed, whereupon a sparingly soluble sodium salt precipitated. After 3 hours the reaction was complete. The reaction solution was then acidified with 2 N hydrochloric acid. The precipitated acid was suction-filtered and recrystallized from ethyl acetate/cyclohexane.
It had a melting point of 215° C. Yield: 12 g.
41. α-4(4-methylthio-phenoxy)-phenoxy-propionic acid ethyl ester

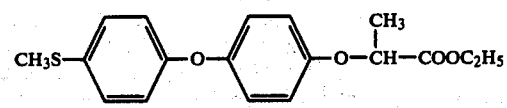

(a) In the same manner as disclosed in Example 40(a), 35 g of 4(4-methylthio-phenoxy)-phenol, 21 g of potassium carbonate, 30 g of α-bromopropionic acid ethyl ester in 500 ml of butanol were reacted. After the work-up there were obtained 30 g of the above-mentioned compound, boiling point: 220°-230°/3-4 mm mercury.
α-4(4-methylthio-phenoxy)-phenoxy-propionic acid

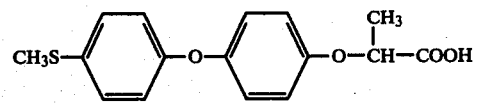

(b) In the same manner as disclosed in Example 40(b), the 30 g of the above-obtained ester were saponified. After the work-up the above-mentioned acid was obtained and recrystallized from benzene/cyclohexane. It had a melting point of 142° C. Yield: 23 g.
42. α-4(4-methylthio-phenoxy)-phenoxy-butyric acid ethyl ester

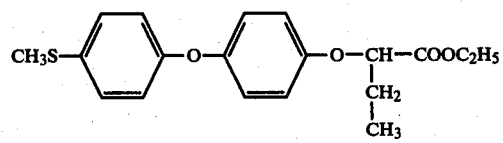

(a) In the same manner as disclosed in Example 40(a), 39 g of 4(4-methylthio-phenoxy)-phenol, 24 g of potassium carbonate, 33 g of α-bromobutyric acid ethyl ester and 500 ml of butanol were reacted. After the work-up, 38 g of the above-mentioned ester were obtained. Boiling point: 220°-235° C./3-4 mm mercury.
(b) α-4(4-methylthio-phenoxy)-phenoxy-butyric acid

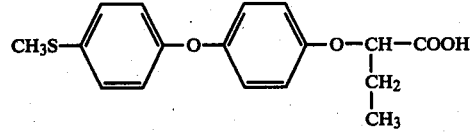

In the same manner as disclosed in Example 40(b), the 39 g of the above-obtained ester were saponified. After the work-up, the acid was first obtained in an oily form. It could be recrystallized from cyclohexane. M.p. 80° C. Yield: 14.5 g.
43. α-4(2,4-dichlorophenoxy)-phenoxy-propionic acid methyl ester A solution of 2550 g of 4-(2,4-dichlorophenoxy)-phenol in xylene is heated with 880 g of 50 percent aqueous sodium hydroxide solution to form the corresponding phenolate. Water is distilled off azotropically and the resulting suspension of phenolate in xylene is heated with 1285 g of methyl 2-chloropropionate for 4 hours at 130°-135° C. After cooling, the inorganic precipitate is extracted with water and xylene is distilled off. The residue is distilled in the high vacuum at 170°-180° C., yielding 3170 g (93% of theory) of methyl 2-[4-(2,4-dichlorophenoxy)-phenoxy]-propionate, B.P. 162°-163° C., (0.13 mbar=0.1 mm Hg).

Preparation of the starting substances according to method (a):

1. 4(4-chloro-3,5-dimethyl-phenoxy)-2,6-dimethyl-anisole

A mixture of 94 g of 4-chloro-3,5-dimethyl-phenol, 129 g of 4-bromo-2,6-dimethyl-anisole, 40 g of potassium hydroxide and 5 g of copper powder was slowly heated to 180°–190° C. During this operation, first the corresponding potassium phenolate formed, and the water formed separated by distillation with a small amount of 4-bromo-2,6-dimethylanisole. At about 200°–220° C., further reaction yielding phenoxy-anisole took place. After about 4 to 5 hours, the reaction was complete. The cooled substance was extracted to exhaustion with a solvent which is not miscible with water, such as methylene chloride. The filtrate of inorganic salts formed was then shaken several times with 2 N sodium hydroxide solution and water. After vaporization of methylene chloride a crude product was obtained which was still contaminated by 4-bromo-2,6-dimethyl-anisole. After distillation, 86 g of 4(4-chloro-3,5-dimethyl-phenoxy)-2,6-dimethyl-anisole were obtained, boiling point: 186° C. under a pressure of 3 mm mercury.

4(4-chloro-3,5-dimethyl-phenoxy)-2,6-dimethyl-phenol 40 g of 4(4-chloro-3,5-dimethyl-phenoxy)-2,6-dimethyl-anisole were added to a solution of 125 ml of 48% hydrobromic acid and 300 ml of glacial acetic acid. The mixture was then refluxed for 2 hours at the reflux condenser. After concentration under reduced pressure, water was added to the residue and the mixture was extracted with methylene chloride. After the organic extract had been shaken several times with water, it was concentrated and the residue was distilled under greatly reduced pressure. 39 g of 4(4-chloro-3,5-dimethyl-phenoxy)-2,6-dimethyl-phenol were obtained, boiling point: 186°–190° C. under a pressure of 2–3 mm mercury.

2. 4(4-Chlorophenoxy)-anisole, boiling point 163°–167° C./4 mm mercury.
4(4-Chlorophenoxy)-phenol, boiling point 174°–176° C./3 mm mercury.

3. 4(4-Methylphenoxy)-anisole, boiling point 157° C./3–4 mm mercury.
4(4-Methylphenoxy)-phenol, boiling point 175°–180° C./3–4 mm mercury.

4. 4(4-Chloro-3,5-dimethylphenoxy)-2,6-dimethylanisole, boiling point 186° C./3–4 mm mercury.
4(4-Chloro-3,5-dimethylphenoxy)-2,6-dimethyl-phenol, boiling point 186°–189° C./2–3 mm mercury.

5. 4(4-Chloro-2-methylphenoxy)-2,6-dimethylanisole, boiling point 178°–180° C./3–4 mm mercury.
4(4-Chloro-2-methylphenoxy)-2,6-dimethylphenol, boiling point 192°–195° C./3–4 mm mercury.

6. 4(4-Chloro-3-methylphenoxy)-anisole, boiling point 167°–170° C./2–3 mm mercury.
4(4-Chloro-3-methylphenoxy)-phenol, boiling point 185°–187° C./2–3 mm mercury.

7. 4(4-Chloro-3,5-dimethylphenoxy)-3,5-dimethylanisole, boiling point 180°–185° C./2–3 mm mercury.
4(4-Chloro-3,5-dimethylphenoxy)-3,5-dimethyl-phenol, boiling point 186°–190° C./2–3 mm mercury.

8. 4(4-Phenylphenoxy)-anisole, m.p. 71° C.
4(4-Phenylphenoxy)-phenol, m.p. 100° C.

9. 4(3,4-Dichlorophenoxy)-anisole, boiling point 177° C./2–3 mm mercury.
4(3,4-Dichlorophenoxy)-phenol, boiling point 187°–190° C./2—3 mm mercury.

10. 4(1-Naphthoxy)-anisole, boiling point 196°–200° C./2–3 mm mercury.
4(1-Naphthoxy)-phenol, boiling point 210°–212° C./2–3 mm mercury.

11. 4(2-Naphthoxy)-anisole, boiling point 200°–205° C./2–3 mm mercury.
4(2-Naphthoxy)-phenol, boiling point 217°–222° C./4–5 mm mercury.

12. 4(2-Isopropyl-5-methylphenoxy)-anisole, boiling point 162° C./2–3 mm mercury.
4(2-Isopropyl-5-methylphenoxy)-phenol, boiling point 170°–171° C./2–3 mm mercury.

13. 4(4-Cyclohexylphenoxy)-anisole, boiling point 204°–208° C./3 mm mercury.
4(4-Cyclohexylphenoxy)-phenol, boiling point 215°–217° C./3 mm mercury.

14. 4(2-Cyclohexylphenoxy)-anisole, boiling point 187°–190° C./3 mm mercury.
4(2-Cyclohexylphenoxy)-phenol, boiling point 200°–205° C./3 mm mercury.

15. 4(2-Cyclohexyl-5-methylphenoxy)-anisole, boiling point 185°–190° C./3 mm mercury.
4(2-Cyclohexyl-5-methylphenoxy)-phenol, boiling point 210°–215° C./3 mm mercury.

16. 4(2(4-Methylcyclohexylphenoxy)-anisole, boiling point 192°–195° C./3 mm mercury.
4(2(4-Methylcyclohexylphenoxy)-phenol, boiling point 205°–210° C./2–3 mm mercury.

17. 4(3,5-Dichlorophenoxy)-anisole, boiling point 170°–190° C./3–4 mm mercury.
4(3,5-Dichlorophenoxy)-phenol, boiling point 192°–195° C./3 mm mercury.

Preparation of the starting substances according to method (b):

1. 4(2,4-Dichloro-phenoxy)-phenol

While stirring, 163 g of 2,4-dichlorophenol and 180 g of 4-chloronitrobenzene were dissolved in 100 ml of dimethylformamide. After addition of 140 g of potassium carbonate and 14 g of copper powder the reaction mixture was refluxed for 4 hours at a reflux condenser. After cooling, the reaction solution was separated from inorganic salts by suction-filtration. Excess dimethylformamide was distilled off under reduced pressure. Methanol was added to the residue, whereupon 235 g of 4(2,4-dichlorophenoxy)-nitrobenzene crystallized, m.p. 74° C. (corrected).

The 235 g of the above-mentioned compound were dissolved in 2.5 l of a mixture of equal volumes of tetrahydrofuran and methanol. After addition of Raney nickel, the solution was shaken under a hydrogen atmosphere. After absorption of the calculated amount of hydrogen, the catalyst was separated from the solution by suction-filtration. Upon concentration 210 g of 4(2,4-dichlorophenoxy)-aniline separated, m.p. 60° C. (corrected).

While heating and stirring, 100 g of 4(2,4-dichloro-phenoxy)-aniline were dissolved in 300 ml of glacial acetic acid. The solution was cooled to 55° C., and 350 ml of 2 N hydrochloric acid were added dropwise. The hydrochloride of aniline separated in finely divided form. Diazotation was performed by adding dropwise 300 ml of 2 N sodium nitrite solution. While stirring was continued 100 ml of 38% hydrofluoboric acid were added in a single portion. The diazonium fluoborate separated, it was suction-filtered and washed with water. 31.5 g of 4(2,4-dichlorophenoxy)-phenol diazonium fluoborate were obtained, m.p. 200° C. (corrected, with decomposition).

While heating and stirring, 135.5 g of 4(2,4-dichlorophenoxy)-phenol diazonium fluoborate were slowly introduced, at about 100°–110° C., into 100 ml of acetic acid anhydride. With a brisk evolution of nitrogen the acetoxy-phenol formed. After about 3 hours the reaction was complete. Excess acetic acid anhydride was distilled off under reduced pressure. The residue was dissolved in 400 ml of methanol and after 100 ml of 45% sodium hydroxide solution had been added, the mixture was refluxed for 2 hours. After vaporization of methanol, the residue was acidified with concentrated hydrochloric acid and extracted with methylene chloride. The extract was washed several times with water and concentrated to dryness under reduced pressure. After distillation under greatly reduced pressure, 66 g of 4(2,4-dichlorophenoxy)-phenol were obtained, m.p. 82° C. (corrected); boiling point: 200°-204° C. under a pressure of 4 mm mercury.

According to an analogous method, the following phenols were obtained:

2. 4(2-chlorophenoxy)-phenol, boiling point: 172°-175° C./2-3 mm mercury,
3. 4(4-chloro-2-cyclopentylphenoxy)-phenol, boiling point: 216°-225° C./4-5 mm mercury,
4. 4(4-chloro-2-cyclohexyl-phenoxy)-phenol, boiling point: 222°-223° C./3 mm mercury,
5. 4(4-methylthio-phenoxy)-phenol, boiling point: 210°-220° C./4-5 mm mercury.

Preparation of the starting substances according to method (c):

4(4-Chlorophenoxy)-2-allyl-phenol 42 g of 4(4-chlorophenoxy)-phenol and 48 g of allyl bromide were heated at the boil at a reflux condenser, while stirring and adding 50 g of potassium carbonate, in 500 ml of butanol for 4 hours. Inorganic salts were then separated from the reaction solution by suction-filtration, the solvent was vaporized and the residue was distilled under greatly reduced pressure. 50 g of 4(4-chlorophenoxy)-phenyl allyl ether were obtained, boiling point: 173°-175° C. under a pressure of 2-3 mm mercury.

50 g of the afore-mentioned allyl ether were heated while stirring to 220°-230° C. During this operation, the rearrangement according to Claisen took place. Distillation under greatly reduced pressure provided 29 g of 4(4-chlorophenoxy)-2-allyl-phenol, boiling point 182°-185° C. under a pressure of 2 mm.

What is claimed is:

1. 4-(2,4-dichlorophenoxy)-phenol and the alkali metal phenolates thereof.

* * * * *